(12) United States Patent
Ben-Levi et al.

(10) Patent No.: US 8,319,978 B2
(45) Date of Patent: Nov. 27, 2012

(54) SYSTEM AND METHOD FOR PROBE MARK ANALYSIS

(75) Inventors: Meir Ben-Levi, Haifa (IL); Ilana Grimberg, Haifa (IL)

(73) Assignee: Camtek Ltd., Migdal Haemek (IL)

(*) Notice: Subject to any disclaimer, the term of this patent is extended or adjusted under 35 U.S.C. 154(b) by 566 days.

(21) Appl. No.: 12/374,316

(22) PCT Filed: Jul. 10, 2007

(86) PCT No.: PCT/IL2007/000859
§ 371 (c)(1),
(2), (4) Date: Mar. 11, 2010

(87) PCT Pub. No.: WO2008/007363
PCT Pub. Date: Jan. 17, 2008

(65) Prior Publication Data
US 2010/0171962 A1    Jul. 8, 2010

Related U.S. Application Data

(60) Provisional application No. 60/806,974, filed on Jul. 11, 2006.

(51) Int. Cl.
*G01B 11/24* (2006.01)
(52) U.S. Cl. .......... 356/608; 356/601; 356/602
(58) Field of Classification Search ........ 356/608–614
See application file for complete search history.

(56) References Cited

U.S. PATENT DOCUMENTS

| | | | | |
|---|---|---|---|---|
| 4,844,617 A * | 7/1989 | Kelderman et al. | ......... | 356/624 |
| 6,248,988 B1 * | 6/2001 | Krantz | ......... | 250/201.3 |
| 6,580,502 B1 * | 6/2003 | Kuwabara | ......... | 356/237.3 |
| 7,787,132 B2 * | 8/2010 | Korner et al. | ......... | 356/601 |
| 7,990,548 B2 * | 8/2011 | Babayoff et al. | ......... | 356/609 |
| 2001/0007498 A1 * | 7/2001 | Arai et al. | ......... | 356/401 |
| 2002/0067490 A1 * | 6/2002 | Okawauchi | ......... | 356/614 |
| 2007/0241266 A1 * | 10/2007 | Gweon et al. | ......... | 250/225 |
| 2008/0100829 A1 * | 5/2008 | Watson | ......... | 356/123 |
| 2008/0100850 A1 * | 5/2008 | Watson | ......... | 356/601 |
| 2008/0151253 A1 * | 6/2008 | Korner et al. | ......... | 356/451 |

* cited by examiner

*Primary Examiner* — Michael P Stafira
(74) *Attorney, Agent, or Firm* — Reches Patents

(57) ABSTRACT

A method for analyzing probe mark, the method includes: scanning the probe mark by multiple spots; evaluating a probe mark characteristic in response to detection signals generated by multiple sensors of the chromatic confocal system that is characterized by a sub-micron axial resolution.

40 Claims, 9 Drawing Sheets

101

SYSTEM AND METHOD FOR PROBE MARK ANALYSIS

RELATED APPLICATIONS

This application claims priority from U.S. provisional patent Ser. No. 60/806974 filed 11 Jul. 2006.

FIELD OF THE INVENTION

The invention relates to probe mark inspection systems and to a method for probe mark analysis.

BACKGROUND OF THE INVENTION

Improvements in Integrated Circuit (IC) performance induced the development of Copper (Cu) and low-K dielectrics. Low-K dielectric materials have a small dielectric constant relative to silicone dioxide ($SiO_2$).

Low-K dielectrics supports higher circuit speed enabling smaller feature sizes by increasing the insulation capability around Copper interconnects. The introduction of Cu low-K dielectric technology presents challenges not only to wafer processing but also to quality and reliability testing and assembling of the integrated circuits.

Compared to the previous generations of silicone dioxide dielectric layers, the low-K layer is characterized by poorer mechanical properties. It can be either softer than a silicone oxide layer or more brittle than the silicone oxide layer. Accordingly, the low-K film is more easily damaged or deformed by a probe that is used to electrically test the integrated circuit. The probes contact integrated circuit test pads and imprint a so-called probe mark on these pads.

The probe marks can affect the functionality of the integrated circuit. For example, deep probe marks can expose a layer that should be buried under the pad. Probe marks can cause shorts or disconnections and effect wire bonding integrity.

Probe marks are relatively shallow and rough and their shape is hard to evaluate. Highly accurate probe mark depth measurements such as atomic force microscope based measurements and focused ion beam cross sectioning based measurements are very costly, very slow and are depending on human interpretation.

Measuring probe mark depth by conventional chromatic confocal systems is very slow and its axial accuracy is limited especially when the chromatic confocal systems are located few centimeters from the wafer.

There is a need to provide a highly accurate high throughput probe mark evaluation method and system.

SUMMARY OF THE INVENTION

A method for analyzing probe mark, the method includes: scanning the probe mark by multiple spots; and evaluating a probe mark characteristic in response to detection signals generated by multiple sensors of the chromatic confocal system that is characterized by a sub-micron axial resolution.

A probe mark inspection system, the system includes: a chromatic confocal system, that comprises multiple sensors and is characterized by a sub-micron axial resolution; wherein the chromatic confocal system is adapted to illuminate the probe mark by multiple spots or single; a translator adapted to scan the probe mark with the multiple spots; and a processor, coupled to the chromatic confocal system; wherein the processor is adapted to evaluate a probe mark characteristic in response to detection signals provided by the chromatic confocal system.

A method for analyzing probe mark, the method includes: scanning a probe mark with a narrow strip of incoherent light along a scan axis that is substantially parallel to a longitudinal axis of the probe mark; wherein the narrow strip is generated by illumination optics that have a large numerical aperture along a longitudinal axis of the strip and a small numerical aperture along a lateral axis of the strip; and evaluating a probe mark characteristic in response to detection signals generated by a sensor of a triangulation system that is characterized by a sub-micron axial resolution; wherein the sensor is preceded by collection optics that are characterized by a large numerical aperture along the longitudinal axis of the strip and a small numerical aperture along the lateral axis of the strip.

A probe mark inspection system, the system includes: a translator adapted to scan the probe mark with a narrow strip of incoherent light along a scan axis that is substantially parallel to a longitudinal axis of the probe mark; illumination optics adapted to illuminate the probe mark with the narrow strip of incoherent light; wherein the illumination optics have a large numerical aperture along a longitudinal axis of the strip and a small numerical aperture along a lateral axis of the strip; collection optics adapted to image the narrow strip of light onto a detector; wherein the collection optics is characterized by a large numerical aperture along the longitudinal axis of the strip and a small numerical aperture along the lateral axis of the strip; and a processor, adapted to evaluate a probe mark characteristic in response to detection signals generated by the sensor; wherein the probe mark inspection system is characterized by a sub-micron axial resolution.

DETAILED DESCRIPTION OF THE DRAWINGS

Chromatic Confocal Embodiment

The basic principle of confocal microscopy is described in U.S. Pat. No. 3,013,467, Minsky. The principle of operation of chromatic confocal systems is illustrated in U.S patent application publication serial number 2005/0030528 of Geffen et al. which is incorporated herein by reference. U.S. Pat. No. 6,573,998 of Cohen-Saban describes a system adapted to perform surface digitization of an object using spatiochromatic triangulation.

Metal pad layer thickness and in consequence probe marks depth are shallow (in most cases are less than a micron).

Accordingly, the chromatic confocal system should have a sub-micron axial resolution. Conveniently, it is also characterized by high lateral resolution. The high lateral resolution is achieved by illuminating the probe mark by small spots and using high numerical aperture chromatic lens. The high axial resolution and hence the high accuracy is achieved by designing the collection optics such that the focus depth of field is narrow. Only the monochromatic wavelength that is sharply focused on the measured object arrives to the filter and enters the spectrometer. The central wavelength of this monochromatic light beam corresponds to the exact height or depth point of the measured object.

The following method and system utilize multiple spots scan a probe mark as well as a pad that includes a probe mark. Although the following description refer to scanning the probe mark those of skill in the art will appreciate that during a scan the probe mark as well as pas areas near the probe mark are scanned.

Figure 1:
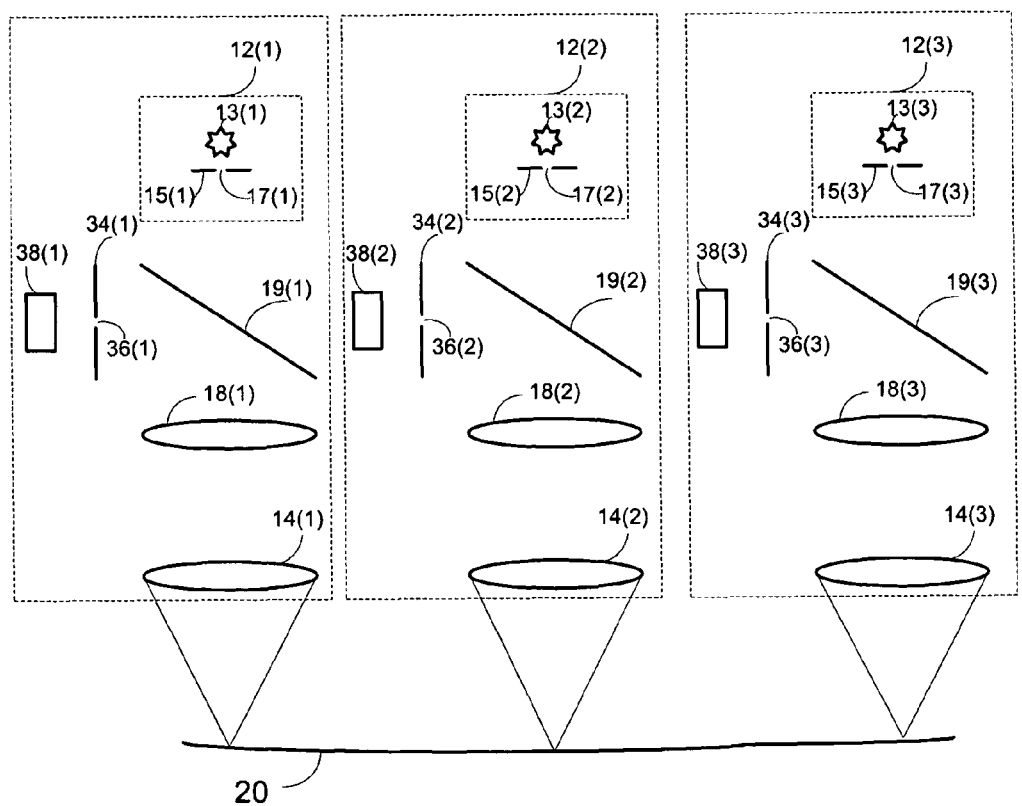
FIG. 1 illustrates a chromatic confocal system according to an embodiment of the invention.

FIG. 1 illustrates chromatic confocal system 10 according to an embodiment of the invention.

For simplicity of explanation FIG. 1 illustrates a chromatic confocal system that illuminates a probe mark by a line of three spots. Chromatic confocal system 10 includes three chromatic confocal pens and three controllers.

It is noted that the number of spots (pens), as well as the spatial relationship between the spots can vary without departing from the scope of the invention.

For example, the spots can form a two dimensional array, can be located closer to each other or more distant from each other, and the like. The spots can form a continuous line, a substantially continuous line, a staggered array, a non-staggered array, a honeycomb shaped array and the like. The pitch between adjacent spots can be very small.

One or more scanning strips can be required in order to scan the whole probe mark or the whole pad on which the probe mark is formed. The scanning can be performed along a scan axis that can be parallel to (or oriented in relation to) a longitudinal axis of the array (or line) formed by the spots of lights. An exemplary scanning scheme can include scanning several lines simultaneously (each line is formed by scanning a single spot) at step size lower than the pitch between light sources and combing the scan strips to the whole scanned area.

Conveniently, the diameter of the spots is small. It can be two microns or even less but this is not necessarily so.

The illumination optics includes non-coherent point light sources 12(1)-12(3), beam splitters 19(1)-19(3), achromatic collimators 18(1)-18(3) and chromatic lenses 14(1)-14(3). Each chromatic lens can separate the non-coherent light beams from a light sources to its basic wavelength beams and focus the basic wavelength beams of light substantially onto a probe mark that belongs to wafer 20.

Point light sources 12(1)-12(3) include three light sources 13(1)-13(3) that are followed by spatial filters 15(1)-15(3), each including a tiny aperture (also referred to as pinhole) 17(1)-17(3) that define the cross section of the light beam. Light that pass through apertures 17(1)-17(3) pass through beam splitters 19(1)-19(3) to be de-magnified by the achromatic collimators 18(1)-18(3), separated to its spectral components (also referred to basic wavelengths) and focused substantially onto the probe mark or the pad on which the probe mark was formed.

Achromatic collimators 18(1)-18(3), chromatic lenses 14(1)-14(3) and beam splitters 17(1)-17(3) are shared by the illumination optics and the collection optics.

The collection optics further includes spatial filters 34(1)-34(3) that define three apertures 36(1)-36(3) and three sensors (also referred to as spectrometers) 38(1)-38(3). Light reflected from probe mark 20 (or the pad on which the probe mark was formed) is collected by chromatic lenses 14(1)-14(3), magnified by achromatic collimators 18(1)-18(3) and are directed by beam splitters 19(1)-19(3) towards apertures 36(1)-36(3) of spatial filters 34(1)-36(3) so that only basic wavelengths that are sharply focused onto the illuminated probe mark are detected by spectrometers 38(1)-38(3).

Each basic wavelength beam has a different focus length. Because chromatic confocal system 10 is absolutely blind for all the space except for the sharply focused spot that illuminates probe mark 20 then the color of light detected by each sensor can provide a highly accurate indication about the depth of the probe mark portion illuminated by the spot. Spectrometers 38(1)-38(3) are highly sensitive to the color of light According to various embodiments of the invention each pair of a chromatic lens and achromatic collimator are arranged in a pen. It is noted that the light source can be included within the controller but this is nit necessarily so. Each pen can be connected to a controller 9 via a fiber. The beam splitter and spatial filter can be located within each controller. The beam splitter, spatial filters, light sources and sensor are located within the controller.

Figure 8:
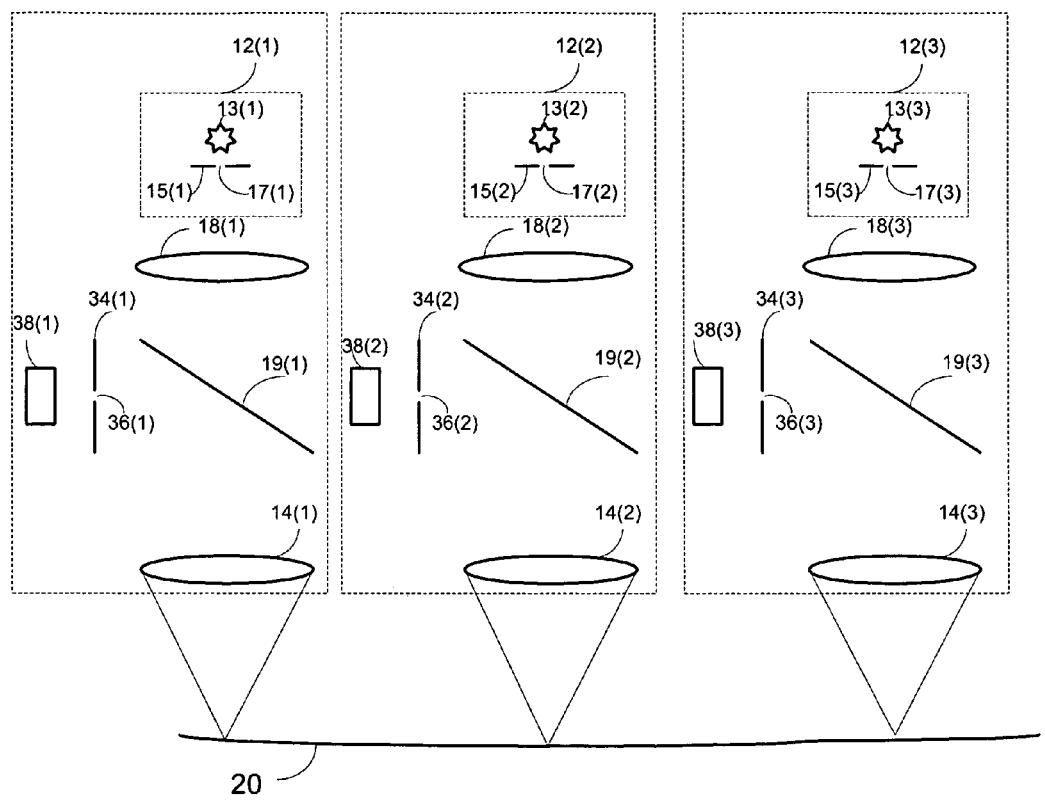
FIG. 8 illustrates a chromatic confocal system according to an embodiment of the invention.

FIG. 8 illustrates chromatic confocal system 10' according to an embodiment of the invention.

System 10' differs from system 10 of FIG. 1 by having achromatic collimators 18(1)-18(3) between the light source 12(1)-12(3) and the beam splitters 19(1)-19(3).

Figure 2:
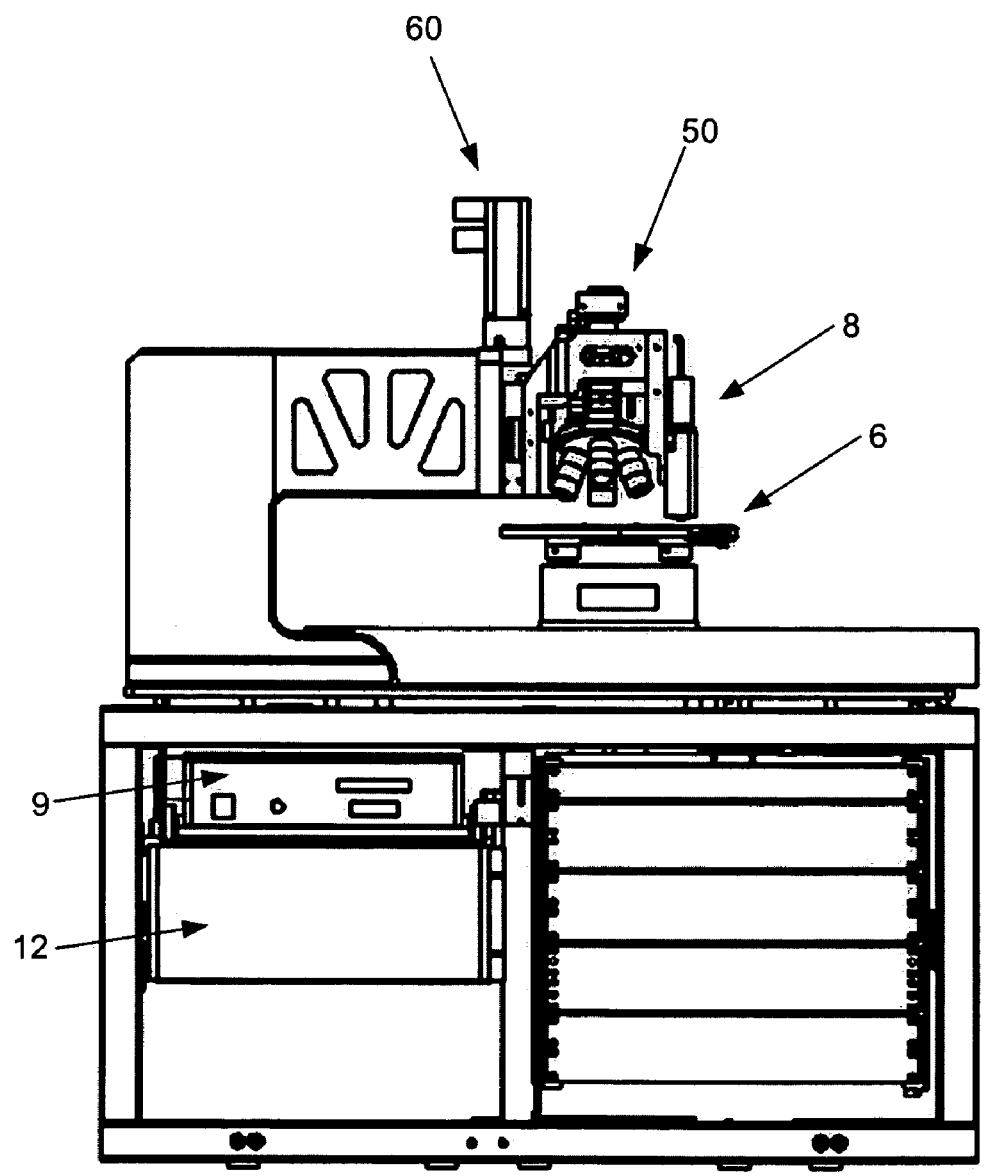
FIG. 2 illustrates a probe mark inspection system according to an embodiment of the invention.

FIG. 2 illustrates probe mark inspection system 100 according to an embodiment of the invention.

Probe mark inspection system 100 includes: (i)

Stage and table that are collectively denoted 6. The table can support wafer 20 while the stage can move the table (and the supported wafer) along imaginary X and Y axes; (ii) chromatic confocal optics 8, (iii) controller 9, (iv) optical head 50, (v) z-axis stage 60, and (vi) processors 12.

Optical head 50 can include an optical microscope as well as one or more cameras that can be used for high speed inspection of wafer 20 and, additionally or alternatively for verification.

Controller 9 can participate in the chromatic confocal process by processing detection signals from chromatic confocal optics 8. Multiple pens can be connected to one or more controllers by multiple fibers, but this is not necessarily so.

Processors 12 controls probe mark inspection system 100 and especially coordinate between the different components of probe mark inspection system 100.

For example, processor 12 can process images acquired by optical head 50 in order to detect probe marks, can process images of probe marks in order to obtain probe marks statistics, can detect suspected probe marks, and the like.

Processors 12 can generate a map of suspected probe marks that are later scanned by chromatic confocal optics 8.

Chromatic confocal optics 8 and controller 9 form chromatic confocal system 10. Optical head 50 and processor 12 form a non-confocal inspection system.

Z-axis stage 60 enables movement in the vertical (Z axis) direction, enabling to elevate and lower the optical head 50 and chromatic confocal optics 8 so that each of them will reach its focal depth of field.

Conveniently, optical head 50 and chromatic confocal optics 8 are aimed to the same point on the wafer that contains the pads and the probe mark 20.

Figure 3:
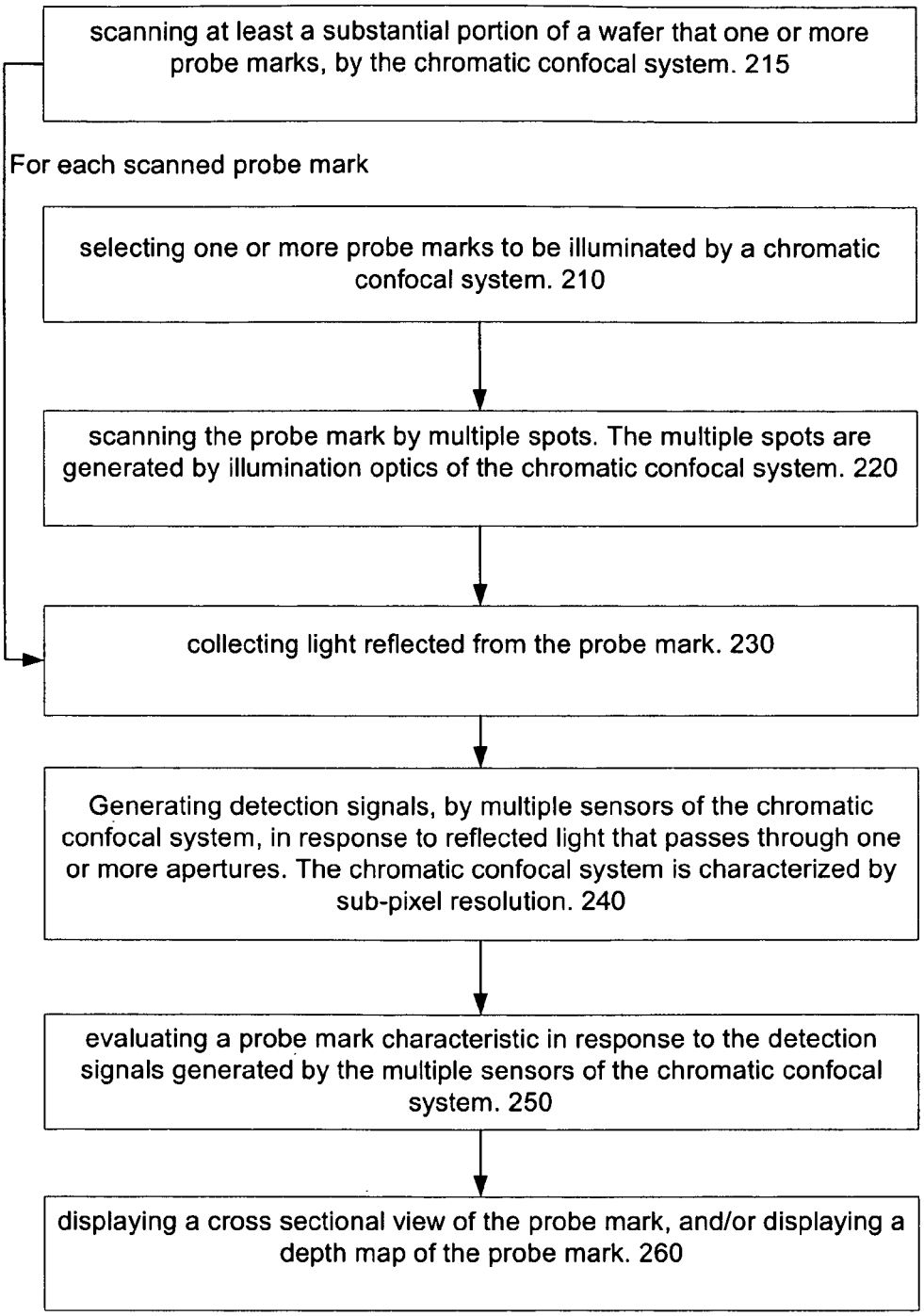
FIG. 3 illustrates a method for probe mark inspection according to an embodiment of the invention.

FIG. 3 illustrates method 200 for probe mark inspection according to an embodiment of the invention.

Method 200 can start by stage 210 or by stage 215.

Stages 210 and 215 can be preceded by the following stages that are not illustrated in FIG. 3 for simplicity of explanation: (i) wafer handling—placing and aligning the wafer on the table before starting the inspection and measurements, (ii) creating a setup and a job—creating (by optical head 50 and processors 12) an image of a die of wafer 20 that includes the pads on which the probe marks were formed, calculating dice indexes, and creating a wafer map showing the dice layout related to the job.

Stage 215 includes scanning at least a substantial portion of a wafer that includes one or more probe marks and pads on which the probe marks were formed, by the chromatic confocal system.

Stage 210 includes selecting one or more probe marks to be illuminated by a chromatic confocal system and scanned The selection can be responsive to results of an inspection of the wafer (or predefined regions of interest or at least a substantial portion of the wafer) by a non-confocal inspection system. The non-confocal inspection system can be faster than the chromatic confocal system but of lower axial resolution. The non-confocal system can be set to a predefined magnification using the optical microscope, reflective or dark field illumination or a combination of both, live black and white and/or color verification cameras.

Images of the wafer can be processed in order to select pads containing probe marks. These can include suspected probe marks. Suspected probe marks can be detected based upon their shape, upon their proximity to pad boundaries, upon their size, probe misalignments, number of touch downs, and even upon to rough estimations about their depth.

According to an embodiment of the invention probe marks statistics can assist in selecting the selected probe marks. These statistics can indicate pads that are more likely to include problematic probe marks.

Yet according to another embodiment of the invention all probe marks of a certain wafer, a certain die, or of a certain area of the wafer are selected. Yet according to another embodiment of the invention the probe marks are selected in an arbitrary manner.

Typically, the selection process can provide a compromise between the speed of probe mark analysis and coverage. Selecting more probe marks will result in a better coverage but can slow the evaluation process.

Stage 220 includes scanning the probe mark by single or multiple spots. The single or multiple spots are generated by illumination optics of the chromatic confocal system.

The scanning can include illuminating the pads containing probe mark by multiple spots and scanning the multiple line spots over the probe mark or over the pad.

The scanning can involve moving the wafer, moving the chromatic confocal system or a combination of both.

Stage 230 includes collecting light reflected from the probe mark. Usually light reflected from the vicinity of the probe mark and the scanned pad (for example portions of the pad that do not include a probe mark).

Stage 240 includes generating detection signals, by multiple sensors of the chromatic confocal system, in response to reflected light that passes through one or more apertures. The chromatic confocal system is characterized by sub-pixel resolution.

Stage 250 includes evaluating a probe mark characteristic in response to the detection signals generated by the multiple sensors of the chromatic confocal system.

The characteristic can include the area of the probe mark, a statistical value that represents the depth of the probe mark, number of probe marks, the shape of the probe mark, proximity of the probe mark to pad boundaries, and the like.

It is noted that method 200 can be executed in a pipelined manner. For example, stage 250 can be executed in parallel to stages 220-240 but can also be executed after the completion of stage 240.

Conveniently, the evaluating includes evaluating the depth of the probe mark portion illuminated by the spots.

According to another embodiment of the invention the multiple spots form a line and stage 230 includes collecting light from the probe mark via a line of apertures.

According to yet another embodiment of the invention each spot is associated with a pen and the light reflected from the probe mark is passed via a fiber towards a pinhole and a detector.

According to another embodiment of the invention the multiple spots form a two dimensional array and stage 230 includes collecting light from the probe mark via a two dimensional array of apertures.

Conveniently, stage 220 utilizes an high numerical aperture illumination optics and stage 230 includes utilizing a high numerical aperture collection optics. The illumination and collection optics are positioned at a substantial working distance from the pad that includes the probe mark.

According to an embodiment of the invention stage 250 can include generating probe mark statistics. The statistics can be updated during each iteration of stage 250 so that after multiple probe marks are scanned and evaluated probe mark statistics are provided.

Stage 250 can include generating a depth map of the probe mark. Additionally or alternatively, one or more cross sections of the probe marks in any direction and angle can be generated.

Conveniently, stage 250 is followed by stage 260 of displaying a cross sectional view of the probe mark, and/or displaying a depth map of the probe mark. According to an embodiment of the invention the cross section can be defined by marking the requested cross section on the depth map.

It is noted that the selection of probe marks to be scanned can be done in an automatic or manual manner. A user can define which pad (probe mark) to scan, when to end a scanning process of a certain probe mark, and the like.

Figure 4A:
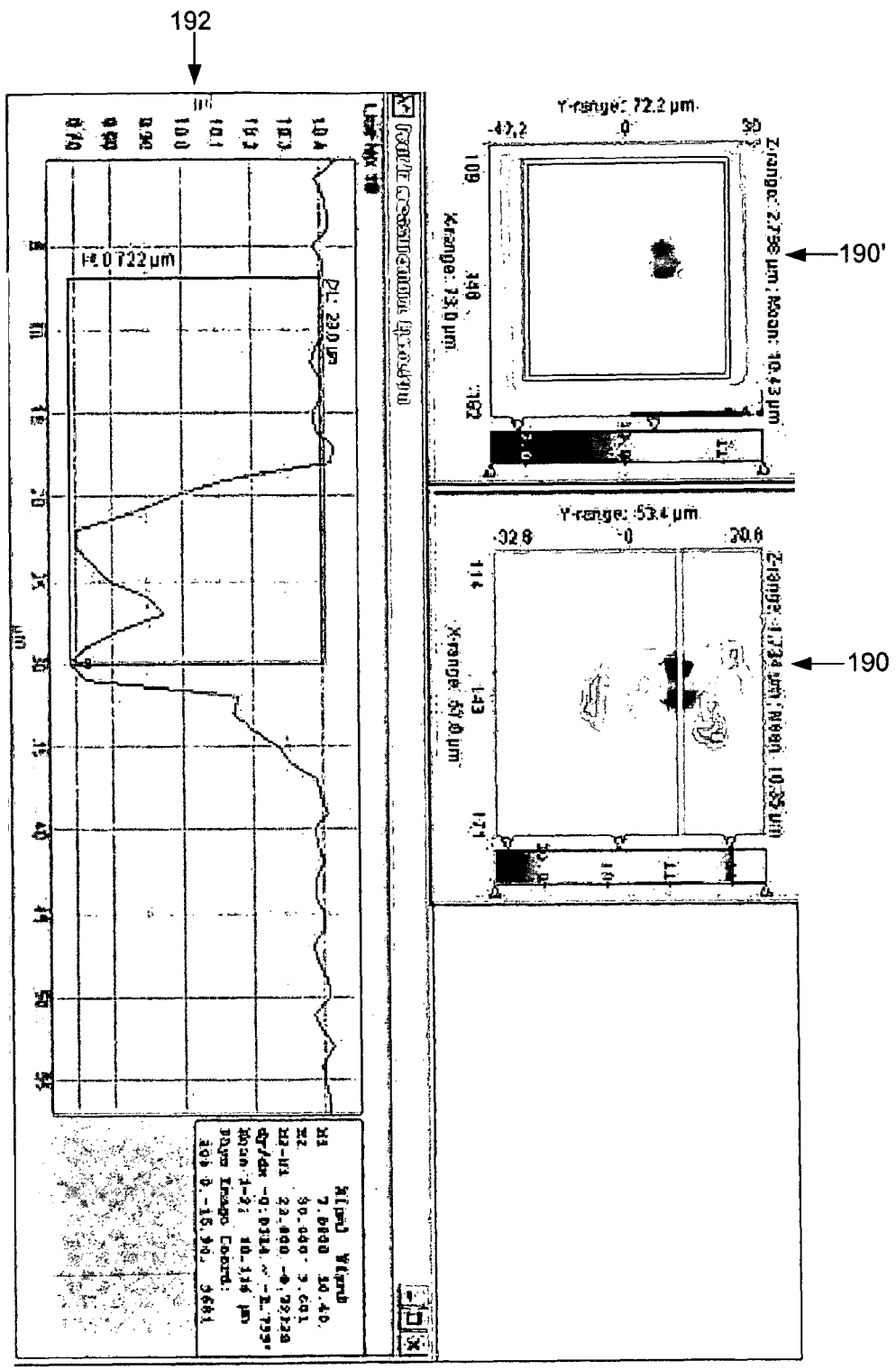
FIGS. 4A and 4B illustrate a probe mark map and a probe mark cross section, according to an embodiment of the invention.
Figure 4B:
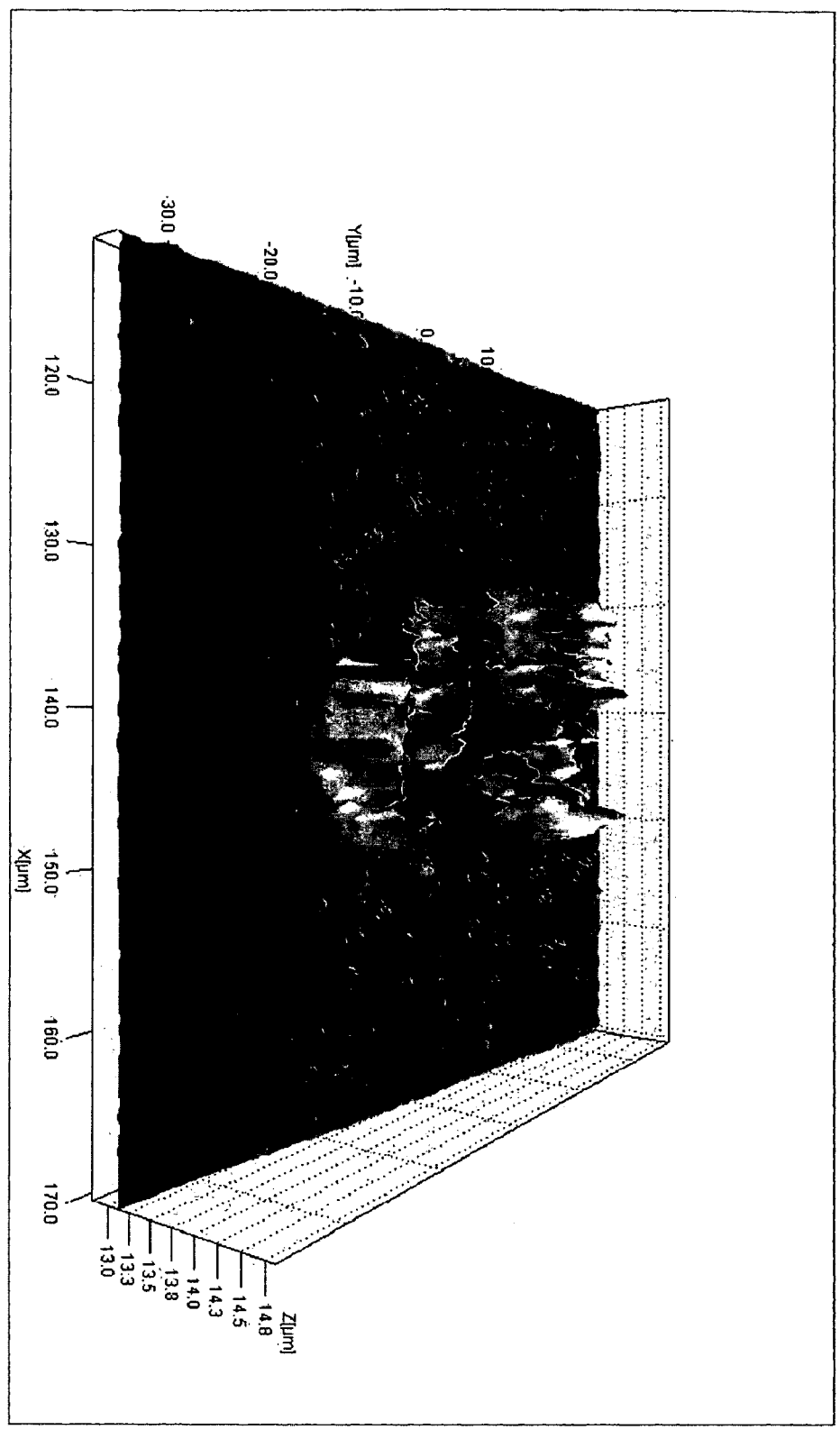

FIGS. 4A-4B illustrates probe mark maps 190 and 190' and a probe mark cross section 192, and a three dimensional map of a probe mark 201 according to an embodiment of the invention. The probe mark cross section 192 can be made along a line that can be determined by defining two points of probe mark map 190. The cross section can be performed along each line and orientation across the pad.

Probe mark map 190 is colorful, while probe mark map 190' is a gray level map. Typically, darker portions (higher gray level pixels) are deeper.

Triangulation System Embodiment

A probe mark inspection system can be equipped with a triangulation system. The triangulation system is asymmetric therefore the direction of scanning is significant to the accuracy of the results.

According to one embodiment of the invention the wafer or the triangulation systems are oriented such that the triangulation system scans the probe mark along a scan axis that is substantially parallel to a longitudinal axis of the probe mark. In many cases the probe marks are relatively long and narrow and their orientation can be determined during a scanning of the wafer by a non-confocal system. The orientation of a probe mark can also be estimated from the orientations of other probe marks, especially from the orientation of probe marks imprinted by the same probe on different pads.

The orientation can involve rotating the wafer. If multiple probe marks are scanned then orientation can be responsive to the orientations of these multiple probe marks. A rotation can be introduced one per wafer, once per probe mark, once per multiple probe marks, once per die, and the like.

Noise that can be associated with scanning the rough probe mark can be reduced by using incoherent illumination and especially broadband illumination such as but not limited to incoherent white light.

A sample configuration of a triangulation system is explained in WO05104658A2 which is incorporated herein by reference.

Figure 5:
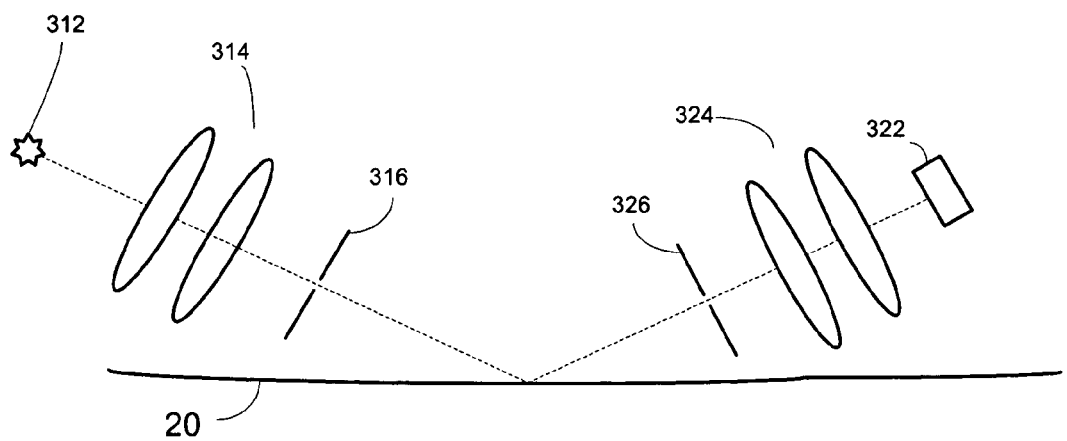
FIG. 5 illustrates a triangulation system according to an embodiment of the invention.

FIG. 5 illustrates triangulation system 300 according to an embodiment of the invention.

Triangulation system 300 includes illumination optics 310 adapted to illuminate the probe mark with a narrow strip of incoherent light.

Illumination optics 310 has a large numerical aperture along a longitudinal axis of the strip and a small numerical aperture along a lateral axis of the strip.

Conveniently, illumination optics 310 includes source of light 312 that is followed by imaging optics 314 and by spatial filter 316. Spatial filter 316 includes a long and narrow aperture. Illumination optics 310 images a strip of light onto the probe mark 320 at a first predefined angle. Imaging optics 314 has a high de-magnification factor and the aperture defined by spatial filter 316 is very narrow thus providing a very narrow strip of light.

Collection optics 320 is adapted to image the narrow strip of light onto detector 330. Collection optics 320 is characterized by a large numerical aperture along the longitudinal axis of the strip and a small numerical aperture along the lateral axis of the strip.

Collection optics 320 includes spatial filter 326 that defines a long and narrow aperture. Spatial filter 326 is followed by imaging optics 324 and detector 330.

Imaging optics 324 have a high magnification factor and the aperture defined by spatial filter 326 is very narrow thus the image of strip on sensor 330 is very narrow (fractions of a micron). Accordingly, a sub-micron axial resolution is obtained even when the triangular system is located at a substantial working distance from the probe mark.

Detector 330 sends detection signals to a processor that is adapted to evaluate a probe mark characteristic in response these detection signals. The height of the illuminated portion of the probe mark can be evaluated by the location of the image of the strip on sensor 330, the illumination angle of illumination optics 310 and the collection angle of collection optics 330.

According to another embodiment of the invention triangulation system 300 includes a set of a beam splitter, light source and detector instead of light source 312 and instead of sensor 330, thus providing two sets of illumination and collection optics. In this embodiment the light sources direct a strip of light towards the beam splitter. The beam splitter directs the strip of light towards the imaging optics and spatial filter. The Beam splitter also allows light reflected from the probe mark to pass through it such as to impinge onto the sensor.

Figure 6:
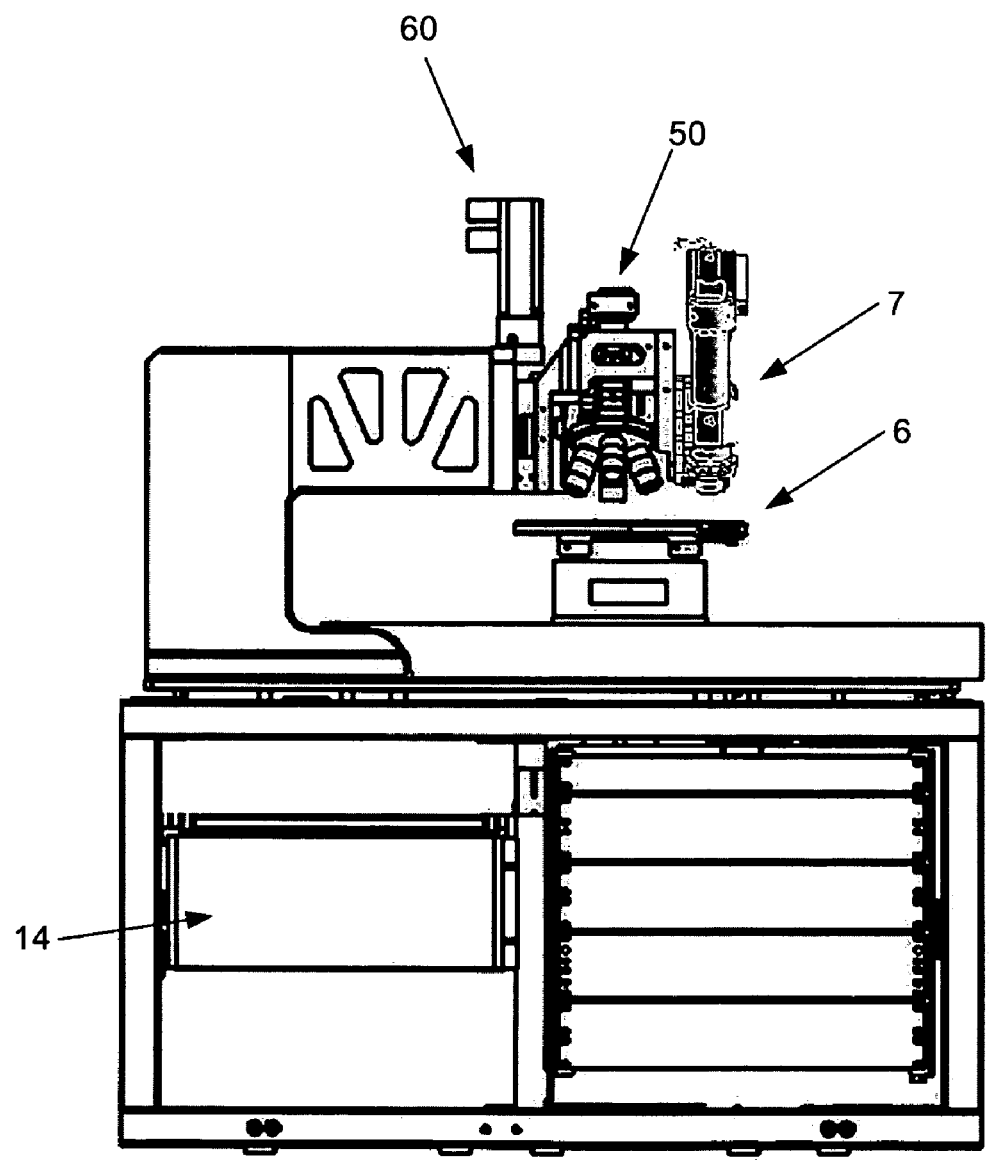
FIG. 6 illustrates a probe mark inspection system according to an embodiment of the invention.

FIG. 6 illustrates probe mark inspection system 101 according to an embodiment of the invention.

Probe mark inspection system 101 includes: (i) Stage and table that are collectively denoted 6. The table can support wafer 20 while the stage can move the table (and the supported wafer) along imaginary X and Y axes; (ii) triangulation system optics 7, (iii) optical head 50, (iv) z-axis transferor stage 60, and (v) processor 12.

Optical head 50 can include an optical microscope as well as one or more cameras that can be used for high speed inspection of wafer 20 and, additionally or alternatively for verification.

Processor 14 can participate in the triangulation process by processing detection signals from a sensor located within or connected to triangulation system optics 7.

Processor 14 can also control probe mark inspection system 101 and especially coordinate between the different components of probe mark inspection system 100.

For example, processor 14 can process images acquired by optical head 50 in order to detect probe marks, can process images of probe marks in order to obtain probe marks statistics, can detect suspected probe marks, and the like.

Processor 14 can generate a map of suspected probe marks that are later scanned by triangulation system optics 7.

Triangulation system optics 7 and processor 14 form triangulation system 300. Optical head 50 and processor 14 form a non-triangulation inspection system.

Z-axis stage 60 enables movement in the vertical (Z axis) direction, enabling to elevate and lower the optical head 50 and triangulation system optics so that each of them will reach its focal depth of field.

Conveniently, optical head 50 and triangulation system optics 7 are aimed to the same point on the wafer 20.

Figure 7:
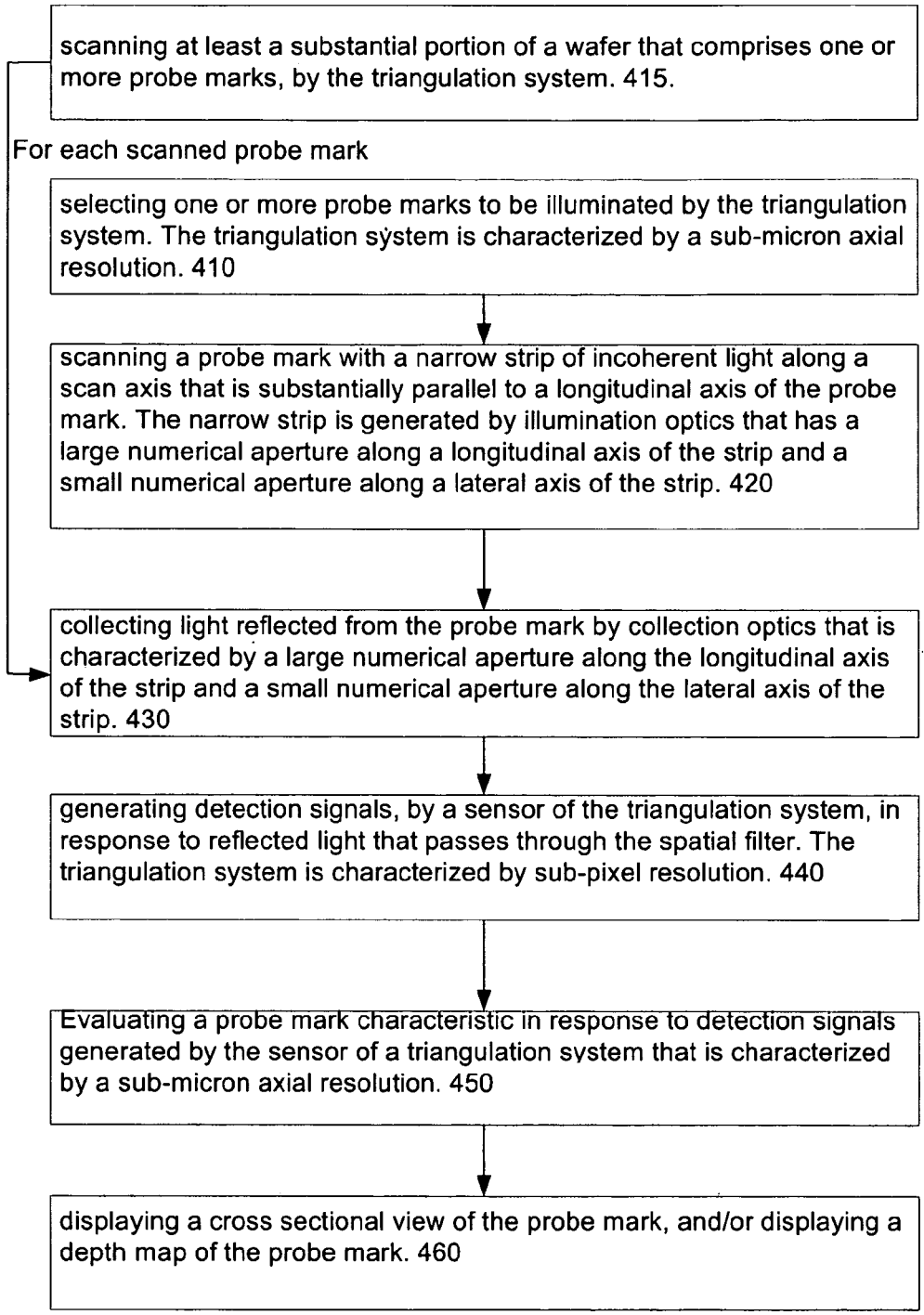
FIG. 7 illustrates a method for probe mark inspection according to an embodiment of the invention.

FIG. 7 illustrates method 400 for probe mark inspection according to an embodiment of the invention.

Method 400 can start by stage 410 or by stage 415.

Stages 410 and 415 can be preceded by the following stages that are not illustrated in FIG. 7 for simplicity of explanation: (i) wafer handling—placing and aligning the wafer on the stage before starting the inspection and measurements, (ii) creating a setup and a job—creating (by optical head 50 and processor 14) an image of a die of wafer 20, calculating dice indexes, and creating a wafer map showing the dice layout related to the job.

Stage 410 includes selecting the probe marks (or pads containing the probe marks) to be illuminated by the triangulation system. The triangulation system is characterized by a sub-micron axial resolution.

For each selected pad containing probe mark, stage 410 is followed by stages 420-450.

Stage 420 includes scanning a probe mark with a narrow strip of incoherent light along a scan axis that is substantially parallel to a longitudinal axis of the probe mark. The narrow strip is generated by illumination optics that has a large numerical aperture along a longitudinal axis of the strip and a small numerical aperture along a lateral axis of the strip.

Stage 430 includes collecting light reflected from the probe mark by collection optics that is characterized by a large numerical aperture along the longitudinal axis of the strip and a small numerical aperture along the lateral axis of the strip.

Stage 440 includes generating detection signals, by a sensor of the triangulation system, in response to reflected light that passes through the spatial filter. The triangulation system is characterized by sub-pixel resolution.

Stage 450 includes evaluating a probe mark characteristic in response to detection signals generated by the sensor of a triangulation system that is characterized by a sub-micron axial resolution.

It is noted that method 400 can be executed in a pipelined manner. For example, stage 450 can be executed in parallel to stages 420-440 but can also be executed after stage 440 is completed.

Stage 415 includes scanning at least a substantial portion of a wafer that comprises one or more probe marks, by the triangulation system.

Conveniently, stage 450 of evaluating includes evaluating the depth of the probe mark portion illuminated by the strip.

According to an embodiment of the invention stage 450 can include generating probe mark statistics. The statistics can be updated during each iteration of stage 450 so that after multiple probe marks are scanned and evaluated probe mark statistics are provided.

Stage 450 can include generating a depth map of the probe mark. Additionally or alternatively, one or more cross sections of the probe marks can be generated.

Conveniently, stage 450 is followed by stage 460 of displaying a cross sectional view of the probe mark, and/or displaying a depth map of the probe mark. According to an embodiment of the invention the cross section can be defined by marking the requested cross section on the depth map.

It is noted that the selection of probe marks to be scanned can be done in an automatic or manual manner. A user can define which probe marks to scan, when to end a scanning process of a certain probe mark, and the like. The user describes which probe marks to scan and the system will scan them automatically. I don't see any point with this high speed system to scan manually.

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

We claim:

1. A method for analyzing probe mark, the method comprising:
    scanning the probe mark by multiple spots; wherein the probe mark is formed on a pad of a wafer by a probe;
    evaluating a probe mark characteristic in response to detection signals generated by multiple sensors of the chromatic confocal system that is characterized by a sub-micron axial resolution, wherein one sensor of the multiple sensors is allocated per spot of the multiple spots.

2. The method according to claim 1 wherein the multiple spots form a line and wherein the method comprises collecting light from the probe mark via a line of apertures.

3. The method according to claim 1 wherein the multiple spots form a two dimensional array wherein the method comprises collecting light from the probe mark via a two dimensional array of apertures.

4. The method according to claim 1 wherein the scanning of the probe mark is preceded by selecting to inspect the probe mark based upon a proximity of the probe mark to boundaries of the pad.

5. The method according to claim 1 comprising scanning at least a substantial portion of the wafer, by a non-confocal inspection system to provide results of an inspection and selecting the probe mark out of multiple probe marks in response to results of the inspection.

6. The method according to claim 1 wherein further comprising scanning at least a substantial portion of the wafer by the chromatic confocal system.

7. The method according to claim 1 further comprising repeating the stage of scanning such as to scan multiple probe marks and wherein the evaluating comprises generating probe mark statistics in response to evaluation of characteristics of the multiple probe marks.

8. The method according to claim 1 further comprising scanning multiple probe marks in response to probe mark statistics.

9. The method according to claim 1 wherein the scanning comprises scanning the probe mark by a chromatic confocal system that is characterized by an axial resolution that is finer than 0.1 micron.

10. The method according to claim 1 wherein the scanning of the probe mark is preceded by selecting the probe mark based upon probe misalignment.

11. The method according to claim 1 further comprising displaying a cross sectional view of the probe mark and a three dimensional map of the probe mark.

12. A probe mark inspection system, the system comprises:
    a chromatic confocal system, that comprises multiple sensors and is characterized by a sub-micron axial resolution; wherein the chromatic confocal system is adapted to illuminate the probe mark by multiple spots; wherein one sensor of the multiple sensors is allocated per spot of the multiple spots; wherein the probe mark is formed on a pad of a wafer by a probe;
    a translator adapted to scan the probe mark with the multiple spots;
    and a processor, coupled to the chromatic confocal system; wherein the processor is adapted to evaluate a probe mark characteristic in response to detection signals provided by the chromatic confocal system.

13. The probe mark inspection system according to claim 12 wherein the chromatic confocal system is adapted to illuminate the probe mark by multiple spots that form a line and wherein the multiple sensors collect light received through a line of apertures.

14. The probe mark inspection system according to claim 12 wherein the chromatic confocal system is adapted to illuminate the probe mark by multiple spots that form a two dimensional array and wherein the multiple sensors collect light received through a two dimensional array of apertures.

15. The probe mark inspection system according to claim 12 further adapted to select a probe mark to be inspected by the confocal inspection system based upon a proximity of the probe mark to boundaries of the pad.

16. The probe mark inspection system according to claim 12 wherein the probe mark inspection system further comprising a non-confocal inspection system adapted to scan at least a substantially portion of a wafer that comprises the probe mark.

17. The probe mark inspection system according to claim 12 further adapted to generate probe mark statistics in response to an evaluation of characteristics of multiple probe marks.

18. The probe mark inspection system according to claim 12 further adapted to scan multiple probe marks in response to probe mark statistics.

19. The probe mark inspection system according to claim 12 wherein the processor is arranged to select the probe mark based upon probe misalignment.

20. The probe mark inspection system according to claim 12 wherein chromatic confocal system is characterized by an axial resolution that is finer than 0.2 micron.

21. The probe mark inspection system according to claim 12 further adapted to display a cross sectional view of the probe mark.

22. A method for analyzing probe mark, the method comprising:
- scanning a probe mark with a narrow strip of incoherent light at an illumination angle and along a scan axis that is substantially parallel to a longitudinal axis of the probe mark; wherein the narrow strip is generated by illumination optics that have a large numerical aperture along a longitudinal axis of the strip and a small numerical aperture along a lateral axis of the strip; and
- evaluating a probe mark characteristic in response to detection signals generated by a sensor of a triangulation system that is characterized by a sub-micron axial resolution; wherein the sensor is preceded by collection optics that are characterized by a large numerical aperture along the longitudinal axis of the strip and a small numerical aperture along the lateral axis of the strip; wherein the collection optics and are arranged to collect light at an collection angle that differs from the illumination angle; wherein the evaluating comprises evaluating a height of an illuminated portion of the probe mark in response to a location of an image of the strip on the sensor, the illumination angle and the collection angle; wherein the probe mark is formed on a pad of a wafer by a probe.

23. The method according to claim 22 wherein the scanning is preceded by rotating the wafer before scanning the probe mark to facilitate the scanning along the scan axis that is substantially parallel to the longitudinal axis of the probe mark.

24. The method according to claim 22 wherein the illumination optics and the collection optics comprises a spatial filter that defines a long and narrow aperture.

25. The method according to claim 22 comprising scanning at least a substantial portion of a wafer that comprises the probe mark, by a non-triangulation inspection system to provide inspection results and selecting at least one probe mark to be inspected in response to the inspection results.

26. The method according to claim 22 further comprising scanning at least a substantial portion of a wafer that comprises the probe mark, by the triangulation system.

27. The method according to claim 22 further comprising repeating the stage of scanning such as to scan multiple probe marks and wherein the evaluating comprises generating probe mark statistics in response to evaluation of characteristics of the multiple probe marks.

28. The method according to claim 22 further comprising scanning multiple probe marks in response to probe mark statistics.

29. The method according to claim 22 wherein the scanning comprises scanning the probe mark by a triangulation system that is characterized by a sub micron axial resolution.

30. The method according to claim 22 wherein the scanning comprises scanning the probe mark by a triangulation system that is characterized by an axial resolution that is finer than 0.2 micron.

31. The method according to claim 22 further comprising displaying a cross sectional view of the probe mark and a three dimensional map of the probe mark.

32. A probe mark inspection system, the system comprises:
- a translator adapted to scan the probe mark with a narrow strip of incoherent light along a scan axis that is substantially parallel to a longitudinal axis of the probe mark;
- illumination optics adapted to illuminate the probe mark with the narrow strip of incoherent light at an illumination angle; wherein the illumination optics have a large numerical aperture along a longitudinal axis of the strip and a small numerical aperture along a lateral axis of the strip;
- collection optics adapted to image the narrow strip of light onto a detector at a collection angle that differs from the illumination angle; wherein the collection optics is characterized by a large numerical aperture along the longitudinal axis of the strip and a small numerical aperture along the lateral axis of the strip; and
- a processor, adapted to evaluate a probe mark characteristic in response to detection signals generated by the sensor; wherein the processor is arranged to evaluate a height of an illuminated portion of the probe mark in response to a location of an image of the strip on the sensor, the illumination angle and the collection angle;
- wherein the probe mark inspection system is characterized by a sub-micron axial resolution.

33. The probe mark inspection system according to claim 32 wherein the translator is arranged to rotate the wafer before the probe mark is inspected to facilitate a scanning of the probe mark along the scan axis that is substantially parallel to the longitudinal axis of the probe mark.

34. The probe mark inspection system according to claim 32 wherein the illumination optics and the collection optics comprises a spatial filter that defines a long and narrow aperture.

35. The probe mark inspection system according to claim 32 adapted to scan at least a substantial portion of a wafer that comprises the probe mark.

36. The probe mark inspection system according to claim 32 further adapted to scan multiple probe marks and to generate probe mark statistics in response to evaluation of characteristics of the multiple probe marks.

37. The probe mark inspection system according to claim 32 further adapted to scan multiple probe marks in response to probe mark statistics.

38. The probe mark inspection system according to claim 32 wherein the illumination optics and the collection optics form a triangulation system that is characterized by an sub-micron axial resolution.

39. The probe mark inspection system according to claim 32 wherein the illumination optics and the collection optics form a triangulation system that is characterized by an axial resolution that is finer than 0.2 micron.

40. The probe mark inspection system according to claim 32 further comprising a display adapted to display a cross sectional view of the probe mark and a three dimensional map of the probe mark.

\* \* \* \* \*